(12) United States Patent
Pratt

(10) Patent No.: US 8,142,625 B2
(45) Date of Patent: Mar. 27, 2012

(54) SYPERHYDROPHOBIC NANOSTRUCTURED MATERIALS AS GAS DIFFUSION ELECTRODES FOR GAS DETECTORS

(75) Inventor: Keith Francis Edwin Pratt, Portsmouth (GB)

(73) Assignee: Life Safety Distribution AG, Uster (CH)

( * ) Notice: Subject to any disclaimer, the term of this patent is extended or adjusted under 35 U.S.C. 154(b) by 380 days.

(21) Appl. No.: 12/431,059

(22) Filed: Apr. 28, 2009

(65) Prior Publication Data

US 2009/0272648 A1      Nov. 5, 2009

Related U.S. Application Data

(60) Provisional application No. 61/049,089, filed on Apr. 30, 2008.

(51) Int. Cl.
*C25B 11/03*   (2006.01)

(52) U.S. Cl. .................. 204/283; 204/284; 204/290.01

(58) Field of Classification Search ............... 204/283, 204/284, 290.01; 428/524, 526, 532, 534
See application file for complete search history.

(56) References Cited

U.S. PATENT DOCUMENTS

| | | | |
|---|---|---|---|
| 4,851,377 A * | 7/1989 | Breault | 502/101 |
| 5,338,430 A | 8/1994 | Parsonage et al. | 204/412 |
| 5,716,507 A * | 2/1998 | Tanaka et al. | 204/424 |
| 7,279,080 B2 | 10/2007 | Chapples et al. | 204/424 |

FOREIGN PATENT DOCUMENTS

| | | |
|---|---|---|
| WO | WO 99/00536 | 7/1999 |
| WO | WO 2004/054015 A2 | 6/2004 |
| WO | WO 2004/054016 A2 | 6/2004 |
| WO | WO 2006/119716 A1 | 11/2006 |

* cited by examiner

*Primary Examiner* — Bruce Bell
(74) *Attorney, Agent, or Firm* — Husch Blackwell LLP

(57) ABSTRACT

An electrochemical gas detector includes a superhydrophobic, nanostructured gas porous electrode. The electrode exhibits a physically disrupted porous region. In an embodiment, electrode material can be deposited around a templating material which is removed before use. Such electrodes exhibit repeatable and reproducible characteristics.

5 Claims, 4 Drawing Sheets

SYPERHYDROPHOBIC NANOSTRUCTURED MATERIALS AS GAS DIFFUSION ELECTRODES FOR GAS DETECTORS

CROSS-REFERENCE TO RELATED APPLICATION

This application claims the benefit of the filing date of U.S. Provisional Application Ser. No. 61/049,089 filed Apr. 30, 2008 and entitled "Superhydrophobic Nanostructured Materials as Gas Diffusion Electrodes".

FIELD

The invention pertains to gas diffusion electrodes. More particularly, the invention pertains to electrochemical gas detectors which include porous gas diffusion electrodes.

BACKGROUND

Gas diffusion electrodes, used for example in electrochemical gas sensors or fuel cells, need a combination of high permeability to gases and controlled permeability to liquid electrolyte, in order to allow target gas access to a three-phase boundary between gas, catalyst and electrolyte, without allowing the electrolyte to leak out or flood the electrode. The desired combination of these properties is typically achieved by supporting the metal catalyst on a porous hydrophobic material (e.g. PTFE), and mixing additives such as PTFE in with the metal particles. (See, for example, "Liquid Electrolyte Fuel Cells", B. S. Hobbs, A. D. S. Tantram & R. Chan-Henry, Ch.6 in "Techniques And Mechanisms In Gas Sensing", Eds. P. T. Moseley, J. O. W. Norris & D. E. Williams, Pub. Adam Hilger, 1991, page 176).

Examples of conventional gas diffusion electrode fabrication techniques include: Puddling: for example, make a low viscosity (typically aqueous) suspension of catalyst and PTFE particles plus other additives such as surfactants, binder etc. spread over PTFE support tape or temporary support such as aluminum foil via pipette/syringe either manually or automatically.

Screen/stencil printing: make a high viscosity mixture of catalyst and PTFE with suitable vehicle (e.g. viscous organic, though aqueous based systems may also be used). Force through screen/stencil to pattern and deposit a defined thickness of material either directly onto PTFE support tape or temporary support.

Manual approach: mix catalyst and PTFE with suitable liquid to make a paste (like mixing cement), then spread over PTFE support tape or temporary support.

In all of the above approaches the electrode mixture may be applied directly to a porous material (e.g. PTFE tape) which will support the electrode when assembled into the sensor, or may be applied to a temporary supporting material such as aluminum foil, and subsequently transferred to the supporting tape. Typically the last step is achieved by pressing. Normally the material will be fired to drive off the carrier.

Disadvantages of this approach are that it is difficult to keep the mixture in suspension. PTFE tends to float to the top, and electrodes can crack under subsequent firing. Therefore constant agitation may be needed in use.

With conventional gas diffusion electrodes, it is very difficult to characterize and control the catalyst properties which affect the overall activity & wetting up. This results in widely varying performance of notionally identical batches. The reliable and repeatable production of gas diffusion electrodes of this type is therefore difficult.

It is desirable to avoid the need to mix a separate hydrophobic material with the catalyst. This can be achieved by making the catalyst itself suitably hydrophobic so that it does not simply saturate with the electrolyte but wets up to a controlled degree, thus maintaining the required mix of gas diffusion paths and wetted electrolyte.

The above results could potentially be achieved by chemically modifying the catalyst surface, but this approach has the undesirable effect of modifying the chemical and electrochemical properties of the material. It is therefore desirable to be able to change the hydrophobicity by a physical means that does not detrimentally affect its chemical properties.

Furthermore, it is also desirable to avoid the need to deposit the catalyst mixture onto a supporting porous tape. Such tapes are, by nature of their construction, fragile and prone to tearing or other damage with the result that electrolyte can potentially leak through them. This effect is worsened by the fact that the hydrophobicity of the catalyst mixture is typically not sufficient to prevent electrolyte coming into contact with the supporting tape. The supporting tape therefore needs to be a material which is chemically compatible with the electrolyte, PTFE is a common choice.

The above could potentially be achieved by utilizing a solid monolithic electrode material thereby removing the need for a support, however this would need to be in the form of a thin porous foil and would not be intrinsically hydrophobic.

It would thus be desirable to be able to manufacture electrodes of the type generally discussed above without the noted disadvantages.

DETAILED DESCRIPTION

Figure 1:
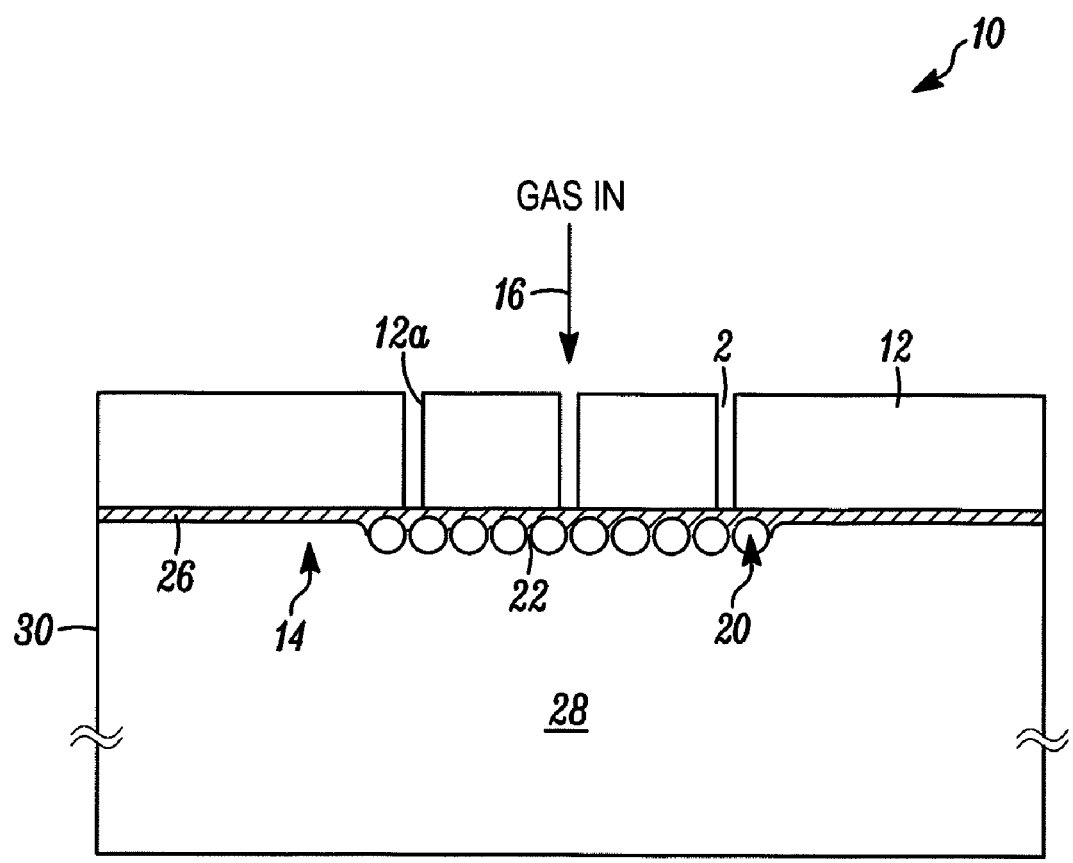
FIG. 1 is a diagram illustrating an exemplary first embodiment of the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention make use of the principle that the hydrophobicity of materials such as metals can be modified by modifying their physical structure at a nanoscale level. This property is known as 'superhydrophobicity' and is described by Cassie's law ("Wettability of porous surfaces", A. B. D. Cassie and S. Baxter, Trans. Faraday Soc., 1944, 40, 546-551. "Superhydrophobic surfaces", Minglin Ma, Randal M. Hill, Current Opinion in Colloid & Interface Science 11 (2006) 193-202).

Such materials could be used in a powder form, whereby the individual powder particles exhibit suitable hydrophobicity that they can be used with the techniques described earlier for manufacturing conventional supported gas diffusion electrodes. The benefit is that a separate phase of hydrophobic material (e.g. PTFE powder) may not need to be mixed with the catalyst in order to produce the required three-phase boundary between catalyst, gas and liquid phases, though it may still be desirable to incorporate a separate phase such as PTFE to provide large scale access of gas through the material or a separate phase of hydrophilic material to maintain wettability.

Using such materials in powder form does not remove the need for a separate material to support the electrode, however this can be achieved by creating a monolithic structure from the superhydrophobic catalyst material, so that the electrode is implemented, for example as one of a porous metal, a metal oxide or carbon foil or layer with appropriate nanostructuring to create both the superhydrophobic property and also be gas permeable.

In an aspect of the invention, since the monolithic structure would have controlled wettability, it could be designed so that the electrolyte would only wet through to a controlled distance. This could allow the structure to comprise two or more laminated metal layers, with one functioning as the electrode catalyst, and the other being on the non-wetted face as a support. As the latter metal is not in contact with the electrolyte it could be a less noble and hence lower cost metal than the electrode material. The latter metal would still require gas porosity to allow gas access to the electrode, but the scale and structure of the porosity does not need to be the same as the electrode. Furthermore, the supporting layer does not need to be metal but could be another material on which the metal electrode could be supported such as a plastic, silicon or ceramic. Chemical compatibility of the material is less critical as it does not contact the electrolyte.

In accordance with the invention, the superhydrophobic nanostructuring and gas porosity can be achieved using various techniques. For example, metal can be electrochemically or chemically deposited around a template comprising self assembled polystyrene or latex spheres. The degree of hydrophobicity is determined both by the size of the templating spheres and the angle subtended between the surface of the metal layer and the walls of the cavities which itself can be controlled by the thickness of the metal layer relative to the diameter of the templating spheres.

In accordance with the invention, if a metal such as gold is electrodeposited around a templating material such as nanosized latex spheres which are subsequently removed, then the resulting metal exhibits 'superhydrophobicity'—i.e. is much more hydrophobic than would normally be expected for the metal. In addition to this unusual property, the metal layer can also be made highly porous, by virtue of the interconnected pores left on removing the template, i.e. very permeable to gases. The template could be removed chemically, for example by dissolution, or thermally by burning or melting all without limitation.

Advantageously, in addition to being unusually hydrophobic, in embodiments of the invention, the degree of hydrophobicity can be tailored by the structure. This is of particular value for gas diffusion electrodes as it allows precise, reliable and mathematically predictable control of the three-phase boundary. Such electrodes can also be tailored to suit the particular electrolyte system being used. This contrasts with the traditional method of electrode formulation by variation of composition such as PTFE loading, and which is somewhat empirical.

In embodiments of the present invention, it is preferable for the material to have gas permeable porosity extending through its thickness. Those of skill in the art will understand that other methods of fabricating materials with the desired properties can also be used. Preferably, they will produce a suitably superhydrophobic surface structure together with gas permeability through the bulk of the material.

In another aspect of the invention, the material combines the desired properties of a precious metal catalyst, gas diffusibility and hydrophobicity, and can also be readily made in the form of a membrane without necessarily requiring an additional supporting structure. An additional benefit is that the templating material can result in a very well defined and repeatable nanostructure—improving electrode repeatability and reproducibility. A further possible benefit is that controlled and repeatable gas diffusion restriction may be tailored into the material allowing it to be used as a diffusion restrictor in addition to or instead of the conventional diffusion restricting capillary or membrane commonly used in electrochemical gas sensors.

In yet another aspect of the invention, nanosized latex spheres (which are commercially and readily available) can be arranged on a suitable sacrificial substrate (eg a metal such as copper). The electrode metal, such as platinum, gold or any other appropriate metal or alloy, is then electroplated around the assembled spheres using methods such as those described in ("Wetting of Regularly Structured Gold Surfaces", M. E. Abdelsalam, P. N. Bartlett, T. Kelf and J. Baumberg, Langmuir 2005, 21, 1753-1757) to produce a suitable hydrophobic surface and appropriate porosity for gas diffusibility. Plating bath additives may be added as appropriate. Alternatively, other templating techniques such as self-assembled surfactant molecules (WO9900536) can be used without departing from the spirit and scope of the invention. The templating material is subsequently removed, for example by dissolving it.

FIG. 1 illustrates one possible example 10 of a dual layer approach where a low cost base metal 12 is used to support the catalyst 14. The base metal 12 needs some form of gas porosity to enable access of the gas from the gas phase 16. In this example the porosity in the support 12 is shown as linear pores 12a, which may be produced, for example, by laser drilling, photolithography or templated electrodeposition (either around latex spheres or self assembled surfactant molecules). The structure of 12 may therefore be similar to templating material 20 and deposition metal 22 or may be in the form of fine capillaries. Either approach has benefits. A very open structure gives minimal restriction to gas access. Conversely, a structure having many fine capillaries could be used as an intentional diffusion restrictor in place of the usual capillary or solid membrane diffusion restriction typically used with electrochemical gas sensors.

The electrode itself with an optional peripheral region 26 and the templated, porous metal region 22 is deposited, for example by electrodeposition on the base metal 12 around templating material 20. The latter is subsequently removed before use. FIG. 1 also shows that the active porous gas accessible electrode region 22 does not need to extend across the whole width of the electrode. There may be a non-porous region 26 around the perimeter of the catalyst 14 to enable electrical contact and also to maximize the contact area with the electrolyte 28 to minimize ohmic losses.

One method of fabricating the structure in FIG. 1 could be to start with a sacrificial metal in place of the gas phase 16, electrodeposit the two metal layers 12 and 14, templating or patterning as required. The sacrificial metal can be removed, for example by chemical dissolution.

FIG. 1 illustrates only a single layer of spherical-like pores in the electrode material. This need not necessarily be the case. Multiple layers come within the spirit and scope of the invention. In FIG. 1 the structure 10 can be combined with a hollow housing 30, electrolyte 28 and other components as would be known to those of skill in the art to form a gas sensor. At least one other electrode needs to be incorporated into the sensor to act as a counter/reference electrode. As this electrode does not necessarily need to be a gas diffusion electrode it may be fabricated by more conventional techniques, however it may also be desirable for this electrode to be nanostructured so as to provide a high surface area. The additional electrode(s) may be separately fabricated or could be coplanar with, but electrically isolated from, the electrode 14. Further additional electrodes may be included as required to act as reference electrodes or secondary sensing electrodes.

Figure 2:
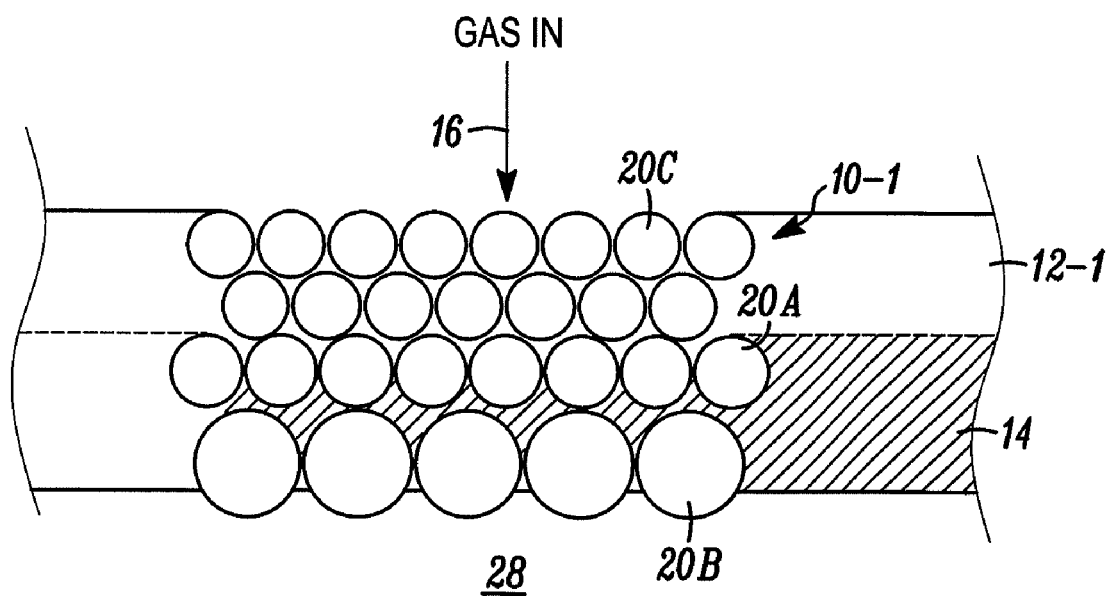
FIG. 2 is a diagram illustrating a second embodiment of the invention.

Additionally, in accordance with embodiments of the invention, the pores do not necessarily need to be monosized. For example, FIG. 2 illustrates schematically two different sizes of pores 20A,B (not to scale). Pores 20A may have the superhydrophobic property, while 20B is fully wetted by the electrolyte 28, producing a large area for contact with the electrolyte. Alternatively, the different sized particles could be mixed (or small particles coated around larger ones) to provide an appropriate mixture of wettability and hydrophobicity through a relatively thick electrode layer. Porosity indicated at 20C can be formed in the support layer 12-1.

Figure 3:
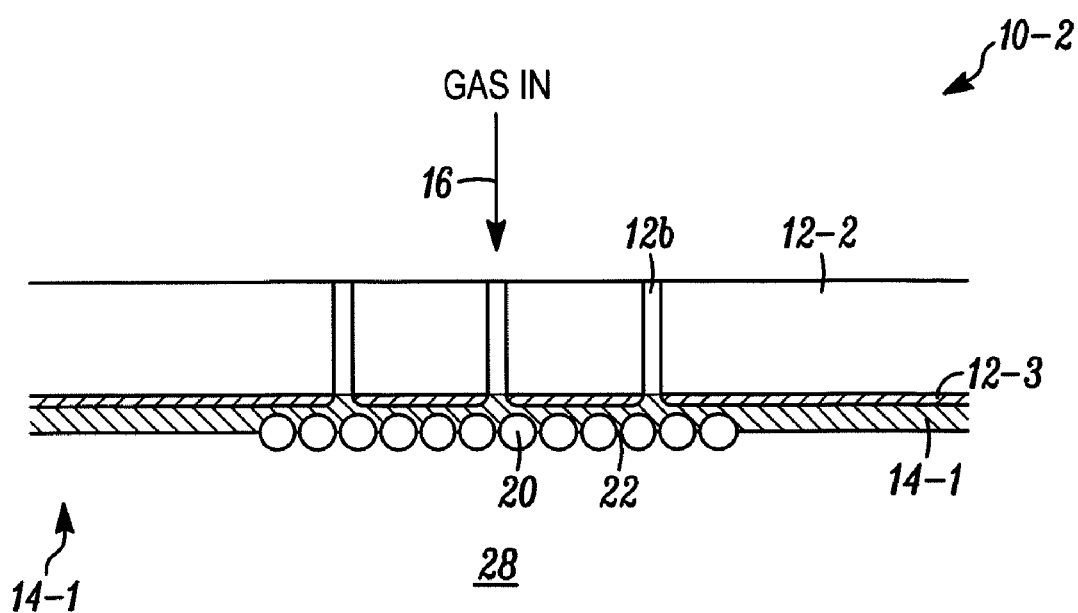
FIG. 3 is a diagram illustrating a third embodiment of the invention.

FIG. 3 shows an alternative approach where the support 12-2 may be electrically insulating. For example, support 12-2 could be formed of a ceramic, plastic or silicon. Pores 12b could be produced by, for example, laser drilling in the case of ceramics or plastics, or by MEMS techniques for silicon. If the electrode 14-1 is to be electrodeposited then an electrically conducting surface 12-3 needs to be produced on the support 12-2. This could be produced by, for example, sputtering or screen printing a metallization layer either before or after producing porosity 12b, or in the case where 12-2 is silicon, an electrically conductive layer may be produced by doping. The templating material 20 is then applied and the electrode 22 electrodeposited as before. A means of external electrical connection to the electrode needs to be provided.

The structure of FIGS. 2, 3 could also be combined with a housing, such as the housing 30, and electrolyte 28 to form a gas sensor. In a further alternative implementation, the porous superhydrophobic material can be used in the form of a powder, which could be used in combination with more conventional electrode fabrication techniques.

Figure 4:
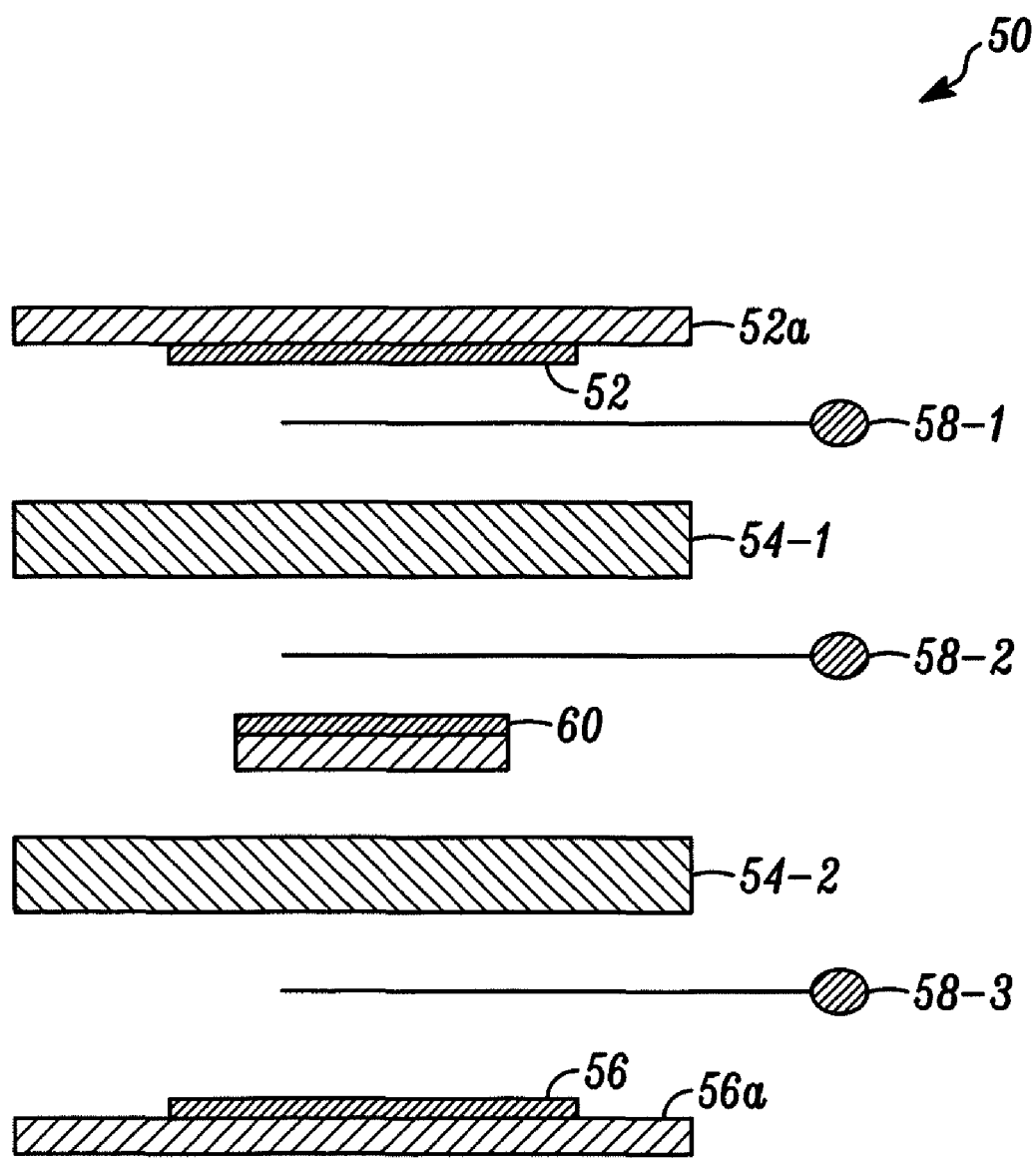
FIG. 4 is a diagram illustrating an electrode structure which embodies the invention.

Gas sensors of a type disclosed in U.S. Pat. No. 7,279,080 issued Oct. 9, 2007 entitled "Gas Sensors" can be implemented with the above described superhydrophobicity. The '080 patent is owned by the assignee hereof and incorporated by reference. FIG. 4 illustrates an exemplary embodiment 50 which includes a porous sensing electrode 52 which exhibits the above described superhydrophobicity achieved by providing a physically disrupted surface region as described above. Electrode 52 is carried by a porous support 52a. Exemplary polymer electrolytes, such as 54-1, -2 space apart current collectors such as 58-1, -2, -3 as well as a counter electrode 56 carried on a support 56a. The structure 50 can be incorporated into a housing, such as housing 30.

Those of skill in the art will understand that embodiments of the invention can incorporate known liquid electrolytes, such as sulfuric acid. Other forms of liquid electrolytes come within the spirit and scope of the invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A structure comprising:
   a porous support with first and second spaced apart surfaces; and
   an electrode carried on one surface, the electrode exhibiting at least one porous, physically disrupted region defined by plurality of spherical-like, interconnecting pores extending into and through a material of the electrode from a side facing away from the support, the layer of pores in the material of the physically disrupted region substantially deteimines the hydrophobicity thereof.

2. A structure as in claim 1 where the support is selected from a class which includes a ceramic, a metal, a plastic, or a semiconductor.

3. A gas diffusion electrode comprising:
   a gas porous layer with a first surface, where porosity extends through the layer, and a catalyst having a physically disrupted region defined by at least a single layer of nanosized spheres disposed on the gas porous layer, depositing a material of the catalyst on the gas porous layer around the nanosized spheres and subsequently removing the nanosized spheres, the removal creating a surface of spherical-like, interconnecting pores in a material of the catalyst which substantially determines the hydrophobicity thereof.

4. An electrode as in claim 3 where the disrupted region comprises a plurality of partially concave depressions.

5. An electrode as in claim 3 where the layer and the region comprise a common material.

* * * * *